United States Patent
Zhou et al.

(10) Patent No.: US 8,450,493 B2
(45) Date of Patent: May 28, 2013

(54) SPIRO PHOSPHINE-OXAZOLINE, PREPARATION METHOD AND APPLICATION THEREOF

(75) Inventors: Qilin Zhou, Tianjin (CN); Shoufei Zhu, Trianjin (CN); Shen Li, Tianjin (CN); Lixin Wang, Tianjin (CN); Song Song, Tianjin (CN)

(73) Assignee: Zheijiang Jiuzhou Pharmaceutical Co., Ltd., Taizhou, Zhejiang (CN)

( * ) Notice: Subject to any disclaimer, the term of this patent is extended or adjusted under 35 U.S.C. 154(b) by 200 days.

(21) Appl. No.: 12/989,610

(22) PCT Filed: Jan. 20, 2009

(86) PCT No.: PCT/CN2009/070229
§ 371 (c)(1),
(2), (4) Date: Oct. 25, 2010

(87) PCT Pub. No.: WO2009/129700
PCT Pub. Date: Oct. 29, 2009

(65) Prior Publication Data
US 2011/0118472 A1 May 19, 2011

(30) Foreign Application Priority Data
Apr. 25, 2008 (CN) .......................... 2008 1 0052879

(51) Int. Cl.
*C07F 15/00* (2006.01)
*C07F 9/653* (2006.01)
*C07C 51/36* (2006.01)

(52) U.S. Cl.
USPC ............................ 548/101; 548/119; 562/496

(58) Field of Classification Search
USPC .................................. 548/101, 119; 562/496
See application file for complete search history.

(56) References Cited

FOREIGN PATENT DOCUMENTS
CN 1884290 A 12/2006

OTHER PUBLICATIONS

Li et al. "Iridium-Catalyzed Enantioselective Hydrogenation of α,β-Unsaturated Carboxylic Acids" Journal of the American Chemical Society, 2008, vol. 130, pp. 8584-8585.*
Li et al. "Iridium-Catalyzed Enantioselective Hydrogenation of α,β-Unsaturated Carboxylic Acids" Journal of the American Chemical Society, 2008, vol. 130, Supporting Information, pp. S1-S58.*
Li, Shen et al.; Iridium-Catalyzed Enantioselective Hydrogenation of a,?-Unsaturated Carboxylic Acids, Journal of the American Chemical Society, Jun. 2008, vol. 130, No. 27, pp. 8584-8585.
Zhu, Shoufei et al.; Well-Defined Chiral Spiro Iridium/Phosphine-Oxazoline Cationic Complexes for Highly Enantioselective Hydrogenation of Imines at Ambient Pressure, Journal of the American Chemical Society, 2006; vol. 128, No. 39, pp. 12886-12891.
Zhang, Zhanhui, Synthesis and Application of Chiral Priro Ligands in Asymmertric Catalysis, Chinese Journal of Organic Chemistry, 2005, vol. 25, No. 4, pp. 355-363.

* cited by examiner

*Primary Examiner* — Joseph Kosack
(74) *Attorney, Agent, or Firm* — Blue Filament Law PLLC; Avery N. Goldstein; Marc Balban

(57) ABSTRACT

The present invention belongs to a spiro phosphine-oxazoline and preparation method and application thereof, particularly, publishes a novel spiro phosphine-oxazoline and the preparation method of its iridium complex. The substituted 7-diaryl phosphino-7'-carboxy-1,1'-Lo-dihydro-indene is used as the starting raw material to synthesize the novel spiro phosphine-oxazoline of the present invention through a two-step reaction. The novel spiro phosphine-oxazoline and the iridium precursor are complexed to become a complex, and then through ion exchange, an iridium/phosphine spiro-oxazoline complex with different anions can be obtained. The present invention overcomes the shortcomings of the existing technology. The cheap readily available amino alcohol is used as the raw material to synthesize the novel spiro phosphine-oxazoline, on the fourth position of the oxazoline ring of which there is no substitutent. The iridium complex of this novel spiro phosphine-oxazoline can catalyze the asymmetric hydrogenation of α-substituted acrylic acid, and shows very high activity and enantioselectivity, therefore has a very high research value and an industrialization prospect.

9 Claims, No Drawings

SPIRO PHOSPHINE-OXAZOLINE, PREPARATION METHOD AND APPLICATION THEREOF

FIELD OF TECHNOLOGY

The present invention relates to a novel spiro phosphine-oxazoline and preparation method and application thereof. Particularly, the substituted 7-diaryl phosphino-7'-carboxyl-1,1'-Lo-dihydro-indene is used as the starting raw material to synthesize the novel spiro phosphine-oxazoline of the present invention through a two-step reaction. The novel spiro phosphine-oxazoline and the iridium precursor are complexed to become a complex, and then through ion exchange, an iridium/phosphine spiro-oxazoline complex with different anions can be obtained. The iridium complex of the novel spiro phosphine-oxazoline can catalyze the asymmetric hydrogenation of α-substituted acrylic acid, and shows very high activity and enantioselectivity.

DESCRIPTION OF RELATED ARTS

Asymmetric catalytic synthesis is a hot spot in the research field of current organic synthetic chemistry (Ohkuma, T.; Kitamura, M.; Noyori, R. *Catalytic Asymmetric Synthesis*, Wiley, New York, 2000). The key of the asymmetric catalytic synthesis is to design and synthesize a chiral catalyst with high enantioselectivity and catalytic activity. The design and synthesis of the chiral catalyst, in a sense, is the design and synthesis of the chiral ligand, as the chiral ligand is the source of the chiral catalyst to generate and control asymmetric induction. In 1966, Wilkinson found a highly active homogeneous catalyst the [Rh(Ph$_3$P)$_3$Cl] complex, providing a premise for the development of asymmetric catalytic hydrogenation (Osborn, J. A.; Jardine, F. H.; Young, J. F.; Wilkinson, G. *J. Chem. Soc. A* 1966, 1711). In 1968, Knowles and Horner reported the first case of metal catalyzed asymmetric catalytic reaction, respectively, (Knowles, W. S.; Sabacky, M. J. *J. Chem. Soc., Chem. Commun.* 1968, 1445; Horner, L.; Siegel, H.; Buthe, H. *Angew. Chem. Int. Ed.* 1968, 7, 942). They introduced chiral phosphine ligands into the Wilkinson catalyst to carry out homogeneous asymmetric catalytic hydrogenations, to obtain 15% ee. This work opened the door of the homogeneous asymmetric catalytic hydrogenation, but also promoted the development of chiral ligands. Up to now, chiral ligands people developed have been up to over a thousand kinds (*Comprehensive Asymmetric Catalysis*; Jacobsen, E N; Pfaltz, A.; Yamamoto, H., Eds.; Springer-Verlag: Heidelberg, 1999).

The Chinese patent CN1884290A published a chiral spiro phosphine-oxazoline ligand SIPHOX with a spiro skeleton structure, the complex catalyst formed by the ligand and iridium has a very high dimensional selectivity to the asymmetric catalytic hydrogenation of imines, and the ee value can be up to 97%, while the complex catalyst has features such as high reactivity and so on. However, for optically pure alkamine-like compounds are used as the raw material of synthesis in the synthesis of the ligand, the synthesis cost of the SIPHOX ligand is relatively high; at the same time, the steric effects of the substituent on the fourth position of the oxazoline ring result in that some substrates can not approach to and coordinate with the metal atoms, reducing the suitable substrate scope of the SIPHOX ligand.

SUMMARY OF THE INVENTION

Aspects of the present invention generally pertain to a spiro phosphine-oxazoline and preparation method and application thereof, so as to be able to overcome the shortcomings of the existing technology. The cheap readily available amino alcohol is used as the raw material to synthesize the novel spiro phosphine-oxazoline, on the fourth position of the oxazoline ring of which there is no substitutent. The iridium complex of this novel spiro phosphine-oxazoline can catalyze the asymmetric hydrogenation of α-substituted acrylic acid, and shows very high activity and enantioselectivity, therefore has a very high research value and an industrialization prospect.

The present invention discloses a spiro phosphine-oxazoline (I), which has the following structure:

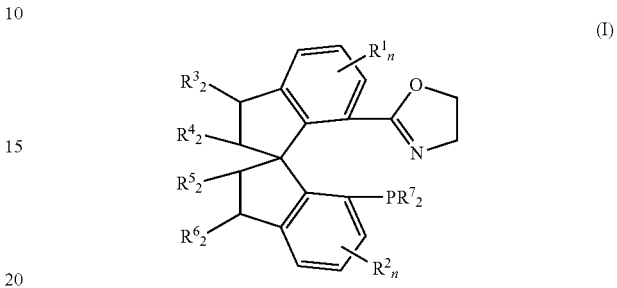

Wherein: n=0~3; $R^1$, $R^2$ are H, $C_1$~$C_8$ alkyl, halogenated alkyl, $C_1$~$C_8$ alkoxy, $C_2$~$C_8$ acyloxy, $C_1$~$C_8$ acyl, $C_2$~$C_8$ esteryl, ($C_1$~$C_8$ acyl) amino, di($C_1$~$C_8$ alkyl) amino, halogen, phenyl, $C_1$~$C_8$ alkyl-substituted phenyl, hydroxyl-substituted phenyl, $C_1$~$C_8$ alkoxy-substituted phenyl, $C_2$~$C_8$ acyloxy-substituted phenyl, halogenated phenyl, amino-substituted phenyl, ($C_1$~$C_8$ acyl) amino-substituted phenyl, di($C_1$~$C_8$ alkyl) amino-substituted phenyl, $C_1$~$C_8$ acyl-substituted phenyl, $C_2$~$C_8$ esteryl-substituted phenyl, naphthyl, furyl, thienyl, or combined alicyclic or aromatic ring (when n≧2), respectively; $R^1$ and $R^2$ can be same or different;

$R^3$, $R^4$, $R^5$, $R^6$ are H, $C_1$~$C_8$ alkyl, halogenated alkyl, $C_1$~$C_8$ alkoxy, $C_2$~$C_8$ acyloxy, $C_1$~$C_8$ acyl, $C_2$~$C_8$ esteryl, ($C_1$~$C_8$ acyl) amino, di($C_1$~$C_8$ alkyl) amino, halogen, phenyl, $C_1$~$C_8$ alkyl-substituted phenyl, hydroxyl-substituted phenyl, $C_1$~$C_8$ alkoxy-substituted phenyl, $C_2$~$C_8$ acyloxy-substituted phenyl, halogenated phenyl, amino-substituted phenyl, ($C_1$~$C_8$ acyl) amino-substituted phenyl, di($C_1$~$C_8$ alkyl) amino-substituted phenyl, $C_1$~$C_8$ acyl-substituted phenyl, $C_2$~$C_8$ esteryl-substituted phenyl, naphthyl, furyl, thienyl, respectively or $R^3$~$R^4$, $R^5$~$R^6$ are combined alicyclic or aromatic ring; $R^3$, $R^4$, $R^5$, $R^6$ can be same or different;

$R^7$ is $C_1$~$C_8$ alkyl, phenyl, $C_1$~$C_8$ alkyl-substituted phenyl, hydroxyl-substituted phenyl, sulfo-substituted phenyl, $C_1$~$C_8$ alkoxy-substituted phenyl, $C_2$~$C_8$ acyloxy-substituted phenyl, halogenated phenyl, amino-substituted phenyl, ($C_1$~$C_8$ acyl) amino-substituted phenyl, di($C_1$~$C_8$ alkyl) amino-substituted phenyl, $C_1$~$C_8$ acyl-substituted phenyl, $C_2$~$C_8$ esteryl-substituted phenyl, naphthyl, furyl, thienyl;

In the spiro phosphine-oxazoline:

The $C_1$~$C_8$ alkyl is methyl, ethyl, n-propyl, isopropyl, cyclopropyl, n-butyl, isobutyl, sec-butyl, tert-butyl, cyclobutyl, pentyl, isoamyl, neopentyl, sec-pentyl, tert pentyl, cyclopentyl, n-hexyl, isohexyl, neohexyl, sec-hexyl, tert-hexyl, cyclohexyl, n-heptyl, isoheptyl, neoheptyl, sec-heptyl, tert-heptyl, cycloheptyl, n-octyl, isooctyl, neooctyl, sec-octyl, tert-octyl or cyclooctyl;

The $C_1$~$C_8$ alkoxy is methoxy, ethoxy, n-propoxy, isopropoxy, cyclopropoxy, n-butoxy, isobutoxy, sec-butoxy, tert-butoxy, cyclobutoxy, n-pentyloxy, isopentyloxy, neopentyloxy, sec-pentyloxy, tert-pentyloxy, cyclopentyloxy, n-hexyloxy, isohexyloxy, neohexyloxy, sec-hexyloxy, tert-hexyloxy, cyclohexyloxy, n-heptyloxy, isoheptyloxy, neoheptyloxy, sec-heptyloxy, tert-heptyloxy, cycloheptyloxy, n-octyloxy, iso-octyloxy, neooctyloxy, sec-octyloxy, tert-octyloxy, cyclooctyloxy;

The $C_1$~$C_8$ acyl is formoxyl, acetyl, propionyl, n-butyryl, isobutyryl, n-valeryl, isovaleryl, sec-valeryl, neovaleryl, n-hexanoyl, isohexanoyl, neohexanoyl, sec-hexanoyl, n-heptanoyl, isoheptanoyl, neoheptanoyl, sec-heptanoyl, n-octanoyl, isooctanoyl, neooctanoyl, sec-octanoyl, 1-cyclopropyl formoxyl, 1-cyclobutyl formoxyl, 1-cyclopentyl formoxyl, 1-cyclohexyl formoxyl, 1-cycloheptyl formoxyl;

The $C_1\sim C_8$ acyloxy is acetoxyl, propionyloxy, n-butyryloxy, isobutyryloxy, n-valeryloxy, isovaleryloxy sec-valeryloxy, neovaleryloxy, n-hexanoyloxy, isohexanoyloxy, neohexanoyloxy, sec-hexanoyloxy, n-heptanoyloxy, isoheptanoyloxy, neoheptanoyloxy, sec-heptanoyloxy, n-octanoyloxy, isooctanoyloxy, neooctanoyloxy, sec-octanoyloxy, 1-cyclopropyl acetoxyl, 1-cyclobutyl acetoxyl, 1-cyclopentyl acetoxyl, 1-cyclohexyl acetoxyl, 1-cycloheptyl acetoxyl;

The $C_2\sim C_8$ esteryl is methoxycarbonyl, ethoxycarbonyl, propoxycarbonyl, isopropoxycarbonyl, butoxycarbonyl, isobutoxycarbonyl, n-pentyloxycarbonyl, isopentyloxycarbonyl, neopentyloxycarbonyl, sec-pentyloxycarbonyl, tert-pentyloxycarbonyl, cyclopentyloxycarbonyl, n-hexyloxycarbonyl, isohexyloxycarbonyl, neohexyloxycarbonyl, sec-hexyloxycarbonyl, tert-hexyloxycarbonyl, cyclohexyloxycarbonyl, n-heptyloxycarbonyl, isoheptyloxycarbonyl, neoheptyloxycarbonyl, sec-heptyloxycarbonyl, tert-heptyloxycarbonyl, cycloheptyloxycarbonyl;

The halogenated alkyl is a halogenated alkyl containing fluoride, chloride, bromine or iodine.

The spiro phosphine-oxazoline contains the raceme, dextroisomer and laevoisomer which have the same chemical structure formula but different three-dimensional structures and optical properties.

The preparation method of the spiro phosphine-oxazoline of the present invention includes the following steps:

At the temperature of 0~60° C., in an organic solvent (one or several of tetrahydrofuran, dioxane, tert-butyl methyl ether, ethylene glycol dimethyl ether), under the role of 1-hydroxy benzotriazole (HOBt, 2~4 mol) and N,N-dicyclohexyl carbimide (DCC, 3~6 mop, the substituted 7-diaryl phosphino-7'-carboxy-1,1'-Lo-dihydro-indene used as the starting raw material and amino ethanol (2~4 mol) are condensed for 10~32 h, to obtain the corresponding amide alcohol compound;

Under the catalysis of 5~10 mol % N,N-dimethyl-4-aminopyridine (DMAP), with triethylamine or diisopropyl ethyl amine (2~4 mol) as the acid binding agent, the amide alcohol compound obtained is reacted with the chlorinating reagent (1~1.2 mol) such as methylsulfonyl chloride, p-toluene sulfonyl chloride and so on for 1~12 h, to obtain the novel spiro phosphine-oxazoline, and the solvent used is one or several of dichloromethane, chloroform or 1,2-dichloroethane, the reaction temperature is 0~25° C., the specific reaction is:

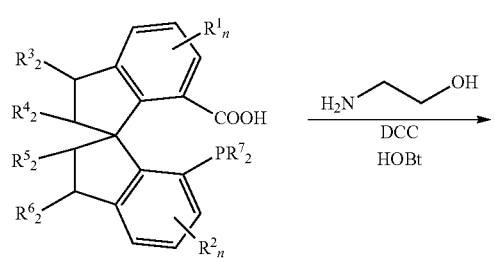

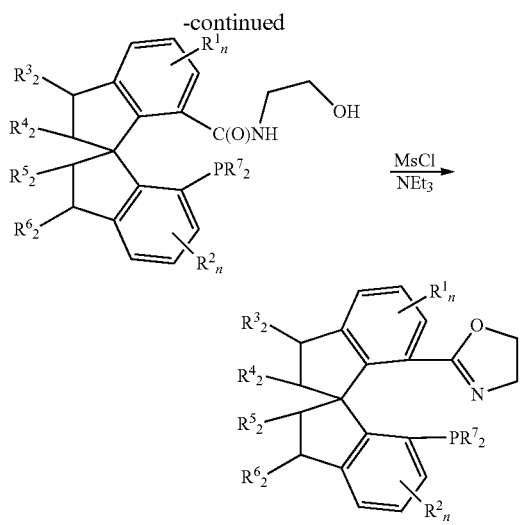

Wherein n=0~3; $R^1$, $R^2$, $R^3$, $R^4$, $R^5$, $R^6$, $R^7$ are defined as the compound (I); DCC is N,N-dicyclohexyl carbimide; HOBt is 1-hydroxy benzotriazole; MsCl is methylsulfonyl chloride.

An iridium complex (II) of spiro phosphine-oxazoline prepared with the spiro phosphine-oxazoline provided by the present invention has the following structure:

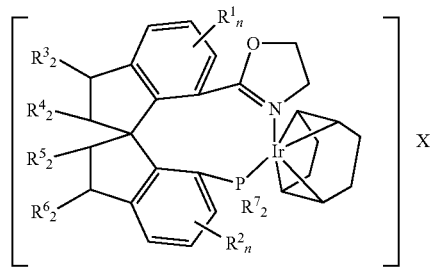

Wherein,

is cyclooctadiene; n=0~3; $R^1$, $R^2$, $R^3$, $R^4$, $R^5$, $R^6$, $R^7$ are defined as the compound (I); X is halogen, $C_1\sim C_8$ carboxylate radical, sulfate radical, tetra(3,5-bis trifluoromethylphenyl) borate radical, tetra(pentafluorophenyl) borate radical, tetra(perfluoro-tert-butoxy) aluminum ion, tetra(hexafluoroisopropoxy) aluminum ion, hexafluoro phosphate ion, hexafluoro antimonlate ion, tetrafluoro borate ion or trifluoro methanesulfonate ion; cyclooctadiene ligand can be substituted by ethylene or norbornadiene; sodium salt may be substituted by corresponding potassium salt, ammonium salt, silver salt or thallium salt.

The preparation of the iridium complex (II) of spiro phosphine-oxazoline is prepared through the following steps: the spiro phosphine-oxazoline (1 mol), a univalent iridium compound such as [Ir(COD)Cl]$_2$ (COD=cyclooctadiene) (0.5~1 mol) and sodium salt (1~3 mol) are reacted at 20~50° C. in the organic solvent (one or several of dichloromethane, chloroform or 1,2-dichloroethane), to obtain the product, and then through ion exchange, an iridium complex of spiro phosphine-oxazoline with different anions can be obtained:

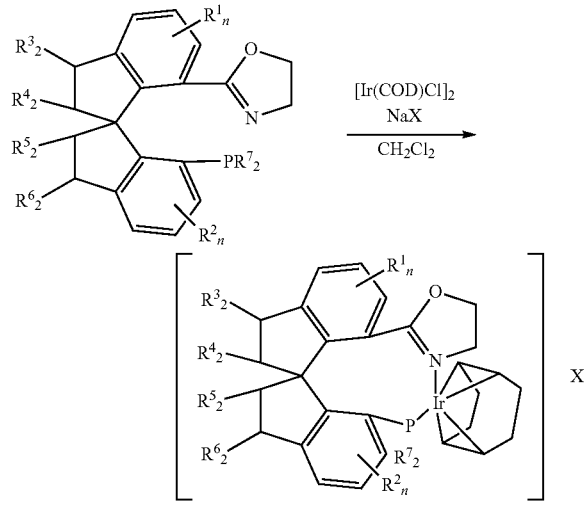

Wherein n=0~3; $R^1$, $R^2$, $R^3$, $R^4$, $R^5$, $R^6$, $R^7$, X are defined as the compounds (I); COD is cyclooctadiene; the cyclooctadiene ligand can be substituted by ethylene or norbornadiene.

The application of the spiro phosphine-oxazoline is to be used to catalyze asymmetric hydrogenation of α-substituted acrylic acid.

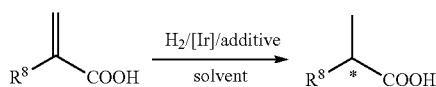

Wherein: [Ir] is the iridium complex of spiro phosphine-oxazoline shown as the formula (II); $R^8$ is halogen, $C_1$~$C_8$ alkyl, halogenated alkyl, $C_1$~$C_8$ alkoxy, benzyloxy, phenoxy, $C_2$~$C_8$ acyloxy, $C_1$~$C_8$ acyl, $C_2$~$C_8$ esteryl, ($C_1$~$C_8$ acyl) amino, di($C_1$~$C_8$ alkyl) amino, benzyl, phenemyl, phenyl, $C_1$~$C_8$ alkyl-substituted phenyl, hydroxyl-substituted phenyl, $C_1$~$C_8$ alkoxy-substituted phenyl, $C_2$~$C_a$ acyloxy-substituted phenyl, halogenated phenyl, amino-substituted phenyl, ($C_1$~$C_8$ acyl) amino-substituted phenyl, di($C_1$~$C_8$ alkyl) amino-substituted phenyl, $C_1$~$C_8$ acyl-substituted phenyl, $C_2$~$C_8$ esteryl-substituted phenyl, naphthyl, furyl, thienyl; the position marked by the asterisk is the chiral center.

The specific process is that: under the protection of argon or nitrogen, the catalyst and the substrate are added into the inner tube of the reactor, then the additive and the solvent are added, the reactor is sealed and the air in the reactor is replaced with hydrogen for 3 to 5 times, then the reactor is filled with hydrogen, and the mixture is stirred to the end;

The catalytic hydrogenation reaction condition is that: the solvent used is $C_1$~$C_6$ alcohol; the amount of the catalyst is 0.001~1 mol %; the concentration of the substrate is 0.001~10.0 M; the additive is one or several of isopropylamine, tert-butylamine, dimethylamine, diethyl amine, diisopropylamine, diisopropyl ethylamine, trimethylamine, triethylamine, 1,8-diazabicyclo[5,4,0]undec-7-ene, 1,4-diazabicyclo[2,2,2]octane, sodium hydride, sodium hydroxide, sodium carbonate, sodium bicarbonate, sodium tert-butyl alcohol, potassium hydroxide, potassium carbonate, potassium bicarbonate, potassium tert-butyl alcohol, cesium hydroxide, cesium carbonate; the reaction temperature is 0~100° C.; the hydrogen pressure is 0.1~10 Mpa; the reaction time is 0.5~48 h.

The present invention provides a spiro phosphine-oxazoline and preparation method and application thereof, which can overcome the shortcomings of the existing technology. The cheap readily available amino alcohol is used as the raw material to synthesize the novel spiro phosphine-oxazoline, on the fourth position of the oxazoline ring of which there is no substitutent. This novel spiro phosphine-oxazoline can catalyze the asymmetric hydrogenation of α-substituted acrylic acid, and shows very high activity and enantioselectivity, therefore has a very high research value and an industrialization prospect.

DETAILED DESCRIPTION OF THE PREFERRED EMBODIMENT

The following embodiments will facilitate to further understand the present invention, but do not limit the contents of the present invention. The preparation method of the present invention can be shown further with the representative compounds as follows:

General Explanation:

The following abbreviations are used in the embodiments, and their meanings are as follows:

Me is methyl, $^t$Bu is tert-butyl, Ph is phenyl, Bn is benzyl, An is p-methoxyphenyl, Xyl is 3,5-dimethylphenyl, DMM is 3,5-dimethyl-4-methoxyphenyl, DTB is 3,5-di-tert-butylphenyl, BARF− is tetra(3,5-bis trifluoromethylphenyl) borate radical; NMR is nuclear magnetic resonance, the chiral SFC is a supercritical fluid chromatography equipped with a chiral column, the chiral GC is a gas chromatography equipped with a chiral capillary column; the ee value is the excess value of enantiomer.

The solvents used are purified and dried with the standard operation before use; the reagents used are commercially available or synthesized according to the existing literature methods and purified before use.

Embodiment 1: Preparation of (Sa)-N-hydroxyethyl-7'-di (3,5-di-tert-butylphenyl)phosphino-1,1'-Lo-dihydro-indene-7-formamide

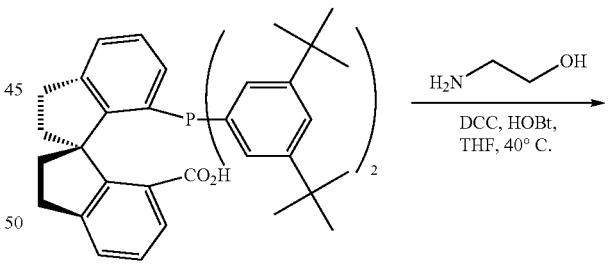

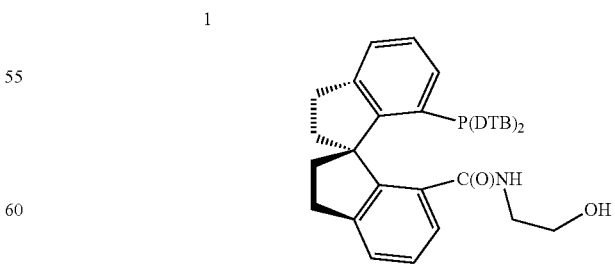

In a 250 mL two-neck flask with anti-stopper, exhaust header and magnetic stirring component, (Sa)-7-di(3,5-ditert-butylphenyl)phosphino-7'-carboxyl-1,1'-Lo-dihydro-indene 1 (1.0 g, 1.48 mmol), amino alcohol (284 mg, 4.65 mmol) and 1-hydroxy benzotriazol (HOBt, 504 mg, 3.29 mmol) and N,N-dicyclohexyl carbimide (DCC, 881 mg, 4.27 mmol) are weighed. Distilled tetrahydrofuran (THF, 80 mL) is added into the above mixture cooled by the ice water, then the temperature rises to the room temperature naturally, the mixture is stirred to react to generate a lot of white precipitation in the system. TLC tracks the reaction until the conversion is completed. Then 5 g silica gel is added, the solvent is evaporated off, then the product is added to the column with dry method, with petroleum ether/ethyl acetate mixed solvent (v/v=1:1) as the eluent for silica gel column chromatography, the compound (Sa)-N-hydroxyethyl-7'-di(3,5-di-tert-butylphenyl)phosphino-1,1'-Lo-dihydro-indene-7-formamide 2 is obtained (660 mg, 62%), which is a white solid. Mp 169~172° C.; $[\alpha]_D^{18}$ −122.6 (c 0.5, CH$_2$Cl$_2$); $^1$H NMR (400 MHz, CDCl$_3$) δ 7.41 (s, 1H, Ar—H), 7.34-7.15 (m, 7H, Ar—H), 7.03 (d, J=8.4 Hz, 2H, Ar—H), 6.71 (d, J=7.6 Hz, 2H, Ar—H), 5.45 (t, J=4.8 Hz, 1H, NH), 3.15-2.76 (m, 9H, OH and CH$_2$), 2.69-2.62 (m, 1H, CH$_2$), 2.43-2.25 (m, 3H, CH$_2$), 1.25 (s, 18H, CH$_3$), 1.18 (s, 18H, CH$_3$); $^{31}$P NMR (162 MHz, CDCl$_3$) δ −16.6 (s); $^{13}$C NMR (100 MHz, CDCl$_3$) δ 171.4, 155.9, 155.7, 151.0, 150.2, 147.5, 146.1, 144.8, 144.7, 138.7, 138.6, 136.5, 136.3, 134.0, 133.8, 133.6, 129.0, 128.7, 127.5, 127.4, 127.3, 127.2, 126.7, 126.5, 126.0, 123.7, 121.7, 63.3, 62.4, 60.6, 43.7, 41.2, 40.8, 35.2, 35.0, 31.6, 31.5, 31.2, 31.0, 21.2, 14.4; HRMS (ESI) calcd for [M+H, C$_{48}$H$_{63}$NO$_2$P]$^+$: 716.4591, Found 716.4590.

The synthesis methods of the following compounds are same to that of Embodiment 1.

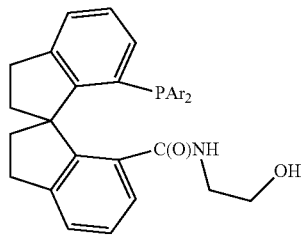

Ar = Ph, 78%
Ar = 4-MeC$_6$H$_4$, 75%
Ar = 4-MeOC$_6$H$_4$, 83%
Ar = 3,5-Me$_2$C$_6$H$_3$, 70%
Ar = 3,4,5-Me$_3$C$_6$H$_2$, 60%
Ar = 3,5-Me$_2$-4-MeOC$_6$H$_2$, 79%
Ar = 3,5-Bu$^t_2$-4-MeOC$_6$H$_2$, 67%

Embodiment 2: Preparation of (Sa)-7-(4,5-dihydro-oxazole-2-base)-7'-di(3,5-di-tert-butylphenyl)phosphino-1,1'-Lo-dihydro-indene

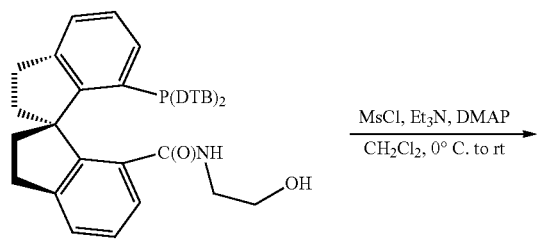

MsCl, Et$_3$N, DMAP
CH$_2$Cl$_2$, 0° C. to rt

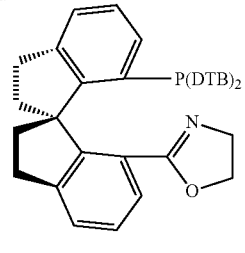

In a 100 mL Schlenk reaction flask with electromagnetic stirring component, (Sa)-N-hydroxyethyl-7'-di(3,5-di-tert-butylphenyl)phosphino-1,1'-Lo-dihydro-indene-7-formamide 2 (660 mg, 0.92 mmol) and 4-dimethylamino pyridine (DMAP, 5 mg, 0.041 mmol) are weighted, the air in the flask is replaced by nitrogen on the vacuum line, then 60 mL dichloromethane degassed after distilled is added, and stirred well. When the mixture is cooled by the ice water, 0.28 mL triethylamine and methylsulfonyl chloride (MsCl, 105 L, 1.36 mmol) are added in turn, the temperature is kept and the mixture is stirred to react for 30 minutes, 1.20 mL triethylamine is added additionally, then the temperature rises to the room temperature naturally, the mixture is stirred overnight. TLC tracks the reaction until the conversion is completed. Then 5 g silica gel is added into the system to quench the reaction, the solvent is evaporated off, then the product is added to the column with dry method, with petroleum ether/ ethyl acetate mixed solvent (v/v=8:1) plus 2% triethylamine as the eluent for column chromatography, the compound (Sa)-7-(4,5-dihydro-oxazole-2-base)-7'-di(3,5-di-tert-butylphenyl)phosphino-1,1'-Lo-dihydro-indene 3 is obtained (463 mg, 72%, which is a white solid. Mp 229~231° C.; $[\alpha]_D^{22}$ −184.4 (c 0.5, CH$_2$Cl$_2$); $^1$H NMR (400 MHz, CDCl$_3$) δ 7.57 (d, J=7.2 Hz, 1H, Ar—H), 7.35-7.20 (m, 5H, Ar—H), 7.06 (t, J=7.6 Hz, 1H, Ar—H), 6.93-6.89 (m, 3H, Ar—H), 6.82 (d, J=8.0 Hz, 2H, Ar—H), 3.75-3.69 (m, 1H, CH$_2$), 3.56-3.50 (m, 1H, CH$_2$), 3.41-3.28 (m, 2H, CH$_2$), 3.06-2.91 (m, 3H, CH$_2$), 2.78-2.69 (m, 2H, CH$_2$), 2.06-2.21 (m, 1H, CH$_2$), 1.99-1.89 (m, 2H, CH$_2$), 1.20 (s, 18H, CH$_3$), 1.17 (s, 18H, CH$_3$); $^{31}$P NMR (162 MHz, CDCl$_3$) δ −15.8 (s); $^{13}$C NMR (100 MHz, CDCl$_3$) δ 165.1, 154.0, 153.8, 150.2, 150.2, 149.9, 149.9, 149.7, 145.2, 144.7, 144.6, 138.0, 137.9, 137.5, 137.4, 133.9, 133.7, 133.0, 128.8, 128.7, 128.6, 128.4, 126.8, 126.7, 126.2, 124.5, 121.8, 121.5, 66.8, 63.5, 54.8, 40.0, 39.3, 35.1, 35.0, 31.7, 31.3, 31.0; HRMS (ESI) calcd for [M+H, C$_{48}$H$_{61}$NOP]$^+$: 698.4485, Found 698.4483.

The synthesis methods of the following compounds are same to that of Embodiment 2.

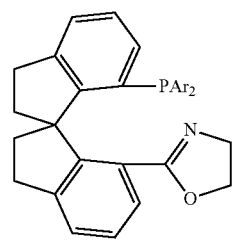

Ar = Ph, 76%
Ar = 4-MeC$_6$H$_4$, 75%
Ar = 4-MeOC$_6$H$_4$, 73%
Ar = 3,5-Me$_2$C$_6$H$_3$, 70%
Ar = 3,4,5-Me$_3$C$_6$H$_2$, 65%
Ar = 3,5-Me$_2$-4-MeOC$_6$H$_2$, 78%
Ar = 3,5-Bu$^t_2$-4-MeOC$_6$H$_2$, 65%

Embodiment 3: Preparation of [(S$_a$-DTB-SIPHOX)Ir(COD)]BARF

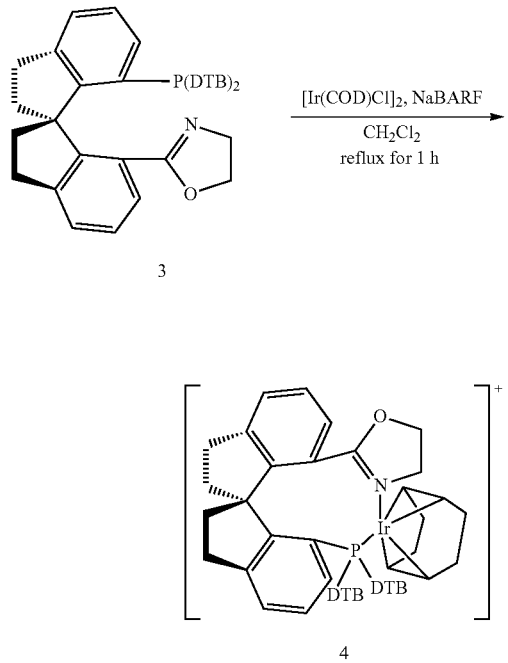

In the glove box, the ligand (Sa)-7-(4,5-dihydro-oxazole-2-base)-7'-di(3,5-di-tert-butylphenyl)phosphino-1,1'-Lo-dihydro-indene 3 (60 mg, 0.085 mmol), [Ir(COD)Cl]$_2$ (32 mg, 0.047 mmol) and NaBARF (100 mg, 0.107 mmol) are weighted into a 15 mL Schlenk reaction flask, when the Schlenk reaction flask is took out, methylene chloride (2 mL) newly distilled is added with a syringe, the mixture is stirred and heated by 45° C. water bath to react for 1 h, the reaction condition is monitored by analyzing the product sample with TLC, when the ligand is complexed completely, heating is stopped, and let the system drop to the room temperature naturally. After the solvent is evaporated off by rotating, [(Sa-DTB-SIPHOX) Ir (COD)] BARF4 (132 mg, 82%) can be obtained by treating the residue with column chromatography, which is an orange foam-shape solid. Mp 196° C.; $[\alpha]_D^{21}$ +122.6 (c 0.5, CH$_2$Cl$_2$); $^1$H NMR (300 MHz, CDCl$_3$) δ 7.65 (brs, 9H, Ar—H), 7.50-7.35 (m, 8H, Ar—H), 7.27-7.24 (m, 1H, Ar—H), 7.18-7.07 (m, 4H, Ar—H), 6.75 (brs, 1H, Ar—H), 6.24 (br d, J=10.8 Hz, 1H, Ar—H), 4.38-4.24 (m, 2H, CH═CH), 3.90-3.63 (m, 3H, CH═CH and CH$_2$), 3.39-3.29 (m, 1H, CH$_2$), 3.16-3.07 (m, 1H, CH$_2$), 2.95-2.56 (m, 4H, CH$_2$), 2.43-2.30 (m, 1H, CH$_2$), 2.08-1.90 (m, 5H, CH$_2$), 1.48-0.80 (m, 40H, CH$_2$ and CH$_3$), 0.47-0.40 (m, 3H, CH$_2$); $^{31}$P NMR (122 MHz, CDCl$_3$) δ 16.7 (s); $^{13}$C NMR (75 MHz, CDCl$_3$) δ 170.9, 162.8, 162.1, 161.5, 160.8, 152.3, 150.9, 150.8, 148.0, 147.9, 147.7, 147.6, 145.5, 143.8, 134.9, 132.3, 132.2, 131.5, 130.9, 130.0, 129.7, 129.2, 128.8, 128.4, 128.0, 127.9, 127.8, 127.7, 127.6, 127.1, 126.9, 126.7, 126.4, 126.3, 124.3, 122.8, 121.1, 119.2, 117.5, 76.7, 71.9, 71.6, 70.7, 70.5, 69.4, 63.1, 51.6, 41.7, 35.0, 34.0, 31.6, 31.5, 31.0, 30.5, 30.2, 29.7, 29.6, 28.8; HRMS (ESI) calcd for C$_{55}$H$_{72}$IrNOP$^+$: 998.4975, Found 998.4977.

The synthesis methods of the following compounds are same to that of Embodiment 3.

Ar = Ph, 81%
Ar = 4-MeC$_6$H$_4$, 83%
Ar = 4-MeOC$_6$H$_4$, 85%
Ar = 3,5-Me$_2$C$_6$H$_3$, 80%
Ar = 3,4,5-Me$_3$C$_6$H$_2$, 71%
Ar = 3,5-Me$_2$-4-MeOC$_6$H$_2$, 85%
Ar = 3,5-Bu$^t_2$-4-MeOC$_6$H$_2$, 82%

Embodiment 4: Asymmetric Synthesis of (R)-ibuprofen

In the glove box, the catalyst [(S$_a$-DTB-SIPHOX)Ir(COD)]BARF 4 (4.7 mg, 0.0025 mmol and 2-(4-isobutylphenyl) acrylic acid 5 (102 mg, 0.5 mmol) are weighted in the reaction inner tube with stirring bar, then the reaction inner tube is sealed for use. When the reaction inner tube is took out, triethylamine (25 mg, 0.25 mmol) and anhydrous methanol (2 mL) are added with a syringe, then the inner tube is placed into the hydrogenation reactor, the mixture is stirred at room temperature under the hydrogen pressure of 0.6 Mpa to react for 24 h. Then the stirring is stopped, the hydrogen is released. After the system is condensed by evaporating off rotatably, the system is adjusted pH<3 with 3N hydrochloric acid water solution, extracted with diethyl ether (10 mL×3), and separated, the organic phase is collected, washed with saturated salt water, and dried with anhydrous sodium sulfate. The desiccant is removed by suction filtration, the solvent is evaporated off by rotating, then the object product 6 is obtained, and is a white solid, through the $^1$H NMR analysis, the conversion rate is 100% and the yield is 96%. Mp 53~55° C.; $[\alpha]_D^{30}$ −41.5 (c 2.0, ethanol); NMR (400 MHz, CDCl$_3$): δ 11.27 (brs, 1H, COOH), 7.24 (d, J=8.4 Hz, 2H, Ar—H), 7.08 (d, J~7.6 Hz, 2H, Ar—H), 3.68 (q, J=6.8 Hz, 1H, CH), 2.43 (d, J=6.8 Hz, 2H, CH$_2$), 1.88-1.78 (m, 1H, CH), 1.48 (d, J=7.2 Hz, 3H, CH$_3$), 0.88 (d, J=6.4 Hz, 6H, CH$_3$); after it is converted to methyl ester, its ee value is 90% through the chiral GC analysis.

Comparative Embodiment 1:

The chiral catalyst

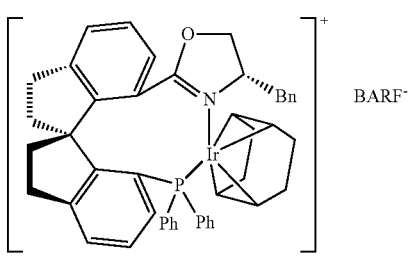

is used, the asymmetric catalytic hydrogenation of 2-(4 isobutyl-phenyl) acrylic acid 5 is carried out under the condition same to that of Embodiment 4, the result of the reaction is that: the conversion rate is 15% and the ee value of the product is 12%.

Comparative Embodiment 2:

The chiral catalyst

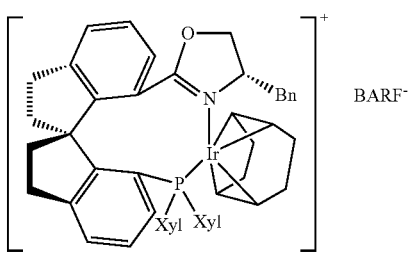

is used, the asymmetric catalytic hydrogenation of 2-(4-isobutyl-phenyl) acrylic acid 5 is carried out under the condition same to that of Embodiment 4, the result of the reaction is that: the conversion rate is 20% and the ee value of the product is 10%.

Comparative Embodiment 3:

The chiral catalyst

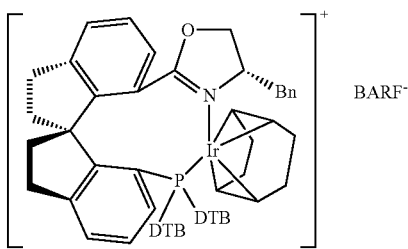

is used, the asymmetric catalytic hydrogenation of 2-(4-isobutyl-phenyl) acrylic acid 5 is carried out under the condition same to that of Embodiment 4, the result of the reaction is that: the conversion rate is 55% and the ee value of the product is 27%.

Comparative Embodiment 4:

The chiral catalyst

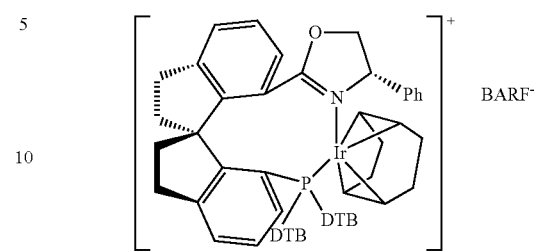

is used, the asymmetric catalytic hydrogenation of 2-(4-isobutyl-phenyl) acrylic acid 5 is carried out under the condition same to that of Embodiment 4, the result of the reaction is that: the conversion rate is 50% and the ee value of the product is 48%.

Comparative Embodiment 5:

The chiral catalyst

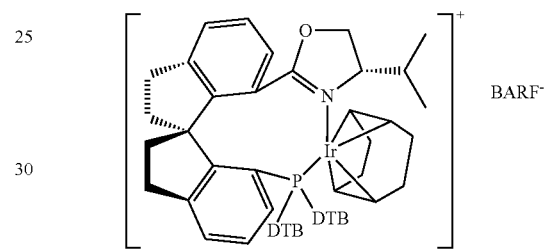

is used, the asymmetric catalytic hydrogenation of 2-(4-isobutyl-phenyl) acrylic acid 5 is carried out under the condition same to that of Embodiment 4, the result of the reaction is that: the conversion rate is 90% and the ee value of the product is 57%.

Comparative Embodiment 6:

The chiral catalyst

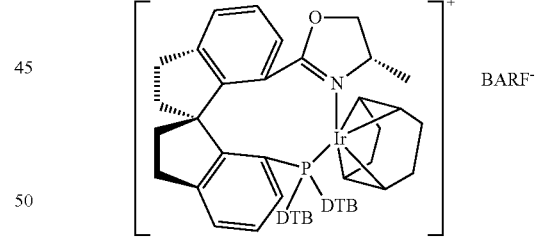

is used, the asymmetric catalytic hydrogenation of 2-(4-isobutyl-phenyl) acrylic acid 5 is carried out under the condition same to that of Embodiment 4, the result of the reaction is that: the conversion rate is 90% and the ee value of the product is 68%.

Embodiment 5: Asymmetric Catalytic Hydrogenation of 2-benzyl acrylic acid

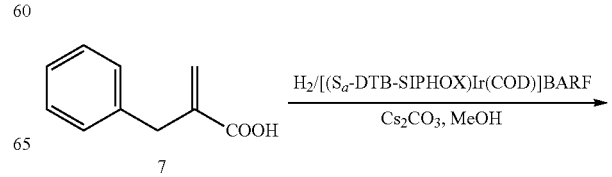

-continued

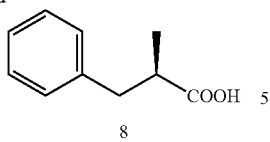
8

In the glove box, the catalyst [(S$_a$-DTB-SIPHOX)Ir(COD)]BARF 4 (2.4 mg, 0.00125 mmol), 2-benzyl acrylic acid 7 (81 mg, 0.5 mmol) and cesium carbonate (82 mg, 0.25 mmol) are weighted in the reaction inner tube with stirring bar, then the reaction inner tube is sealed for use. When the reaction inner tube is took out, anhydrous methanol (2 mL) is added with a syringe, then the inner tube is placed into the hydrogenation reactor, the mixture is stirred at room temperature under the hydrogen pressure of 0.6 Mpa to react for 12 h. Then the stirring is stopped, the hydrogen is released. After the system is condensed by evaporating off rotatably, the system is adjusted pH<3 with 3N hydrochloric acid water solution, extracted with diethyl ether (10 mL×3), and separated, the organic phase is collected, washed with saturated salt water, and dried with anhydrous sodium sulfate. The desiccant is removed by suction filtration, the solvent is evaporated off by rotating, then the object product 8 is obtained, and is a colorless oily liquid, through the $^1$H NMR analysis, the conversion rate is 100% and the yield is 94%. $[\alpha]_D^{30}$ −31.9 (c 1.0, CH$_2$Cl$_2$); $^1$H NMR (400 MHz, CDCl$_3$): δ 9.95 (brs, 1H, COOH), 7.31-7.18 (m, 5H, Ar—H), 3.08 (dd, J=13.2 and 6.4 Hz, 1H, CH$_2$), 2.77 (sextet, J=6.8 Hz, 1H, CH), 2.67 (dd, J=13.2 and 8.0 Hz, 1H, CH$_2$), 1.18 (d, J=6.8 Hz, 3H, CH$_3$); after it is converted to phenyl amide, its ee value is 91% through the chiral SFC analysis.

Comparative Embodiment 1:

The chiral catalyst

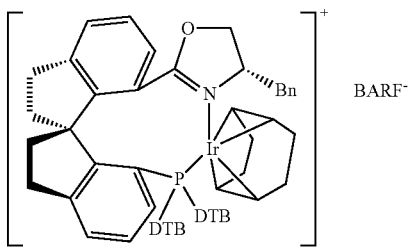

is used, the asymmetric catalytic hydrogenation of 2-benzyl acrylic acid 7 is carried out under the condition same to that of Embodiment 5, the result of the reaction is that: the conversion rate is 100%, the yield is 92% and the ee value of the product is 47%.

Comparative Embodiment 2:

The chiral catalyst

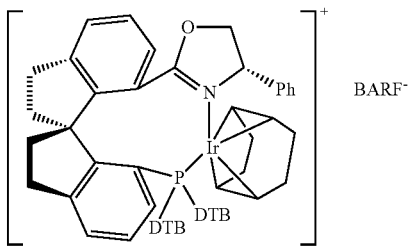

is used, the asymmetric catalytic hydrogenation of 2-benzyl acrylic acid 7 is carried out under the condition same to that of Embodiment 5, the result of the reaction is that: the conversion rate is 100%, the yield is 93% and the ee value of the product is 23%.

Comparative Embodiment 3:

The chiral catalyst

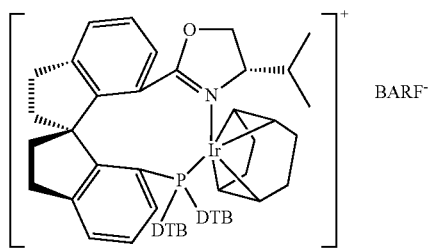

is used, the asymmetric catalytic hydrogenation of 2-benzyl acrylic acid 7 is carried out under the condition same to that of Embodiment 5, the result of the reaction is that: the conversion rate is 100%, the yield is 93% and the ee value of the product is 71%.

Comparative Embodiment 4:

The chiral catalyst

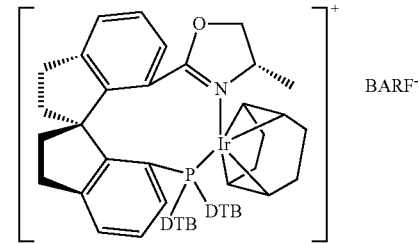

is used, the asymmetric catalytic hydrogenation of 2-benzyl acrylic acid 7 is carried out under the condition same to that of Embodiment 5, the result of the reaction is that: the conversion rate is 100%, the yield is 93% and the ee value of the product is 73%.

Comparative Embodiment 5:

The chiral catalyst

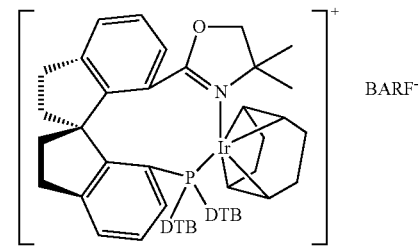

is used, the asymmetric catalytic hydrogenation of 2-benzyl acrylic acid 7 is carried out under the condition same to that of Embodiment 5, the result of the reaction is that: the conversion rate is 10% and the ee value of the product is 21%.

Embodiment 6: Asymmetric Catalytic Hydrogenation of 2-phenylethyl acrylic acid

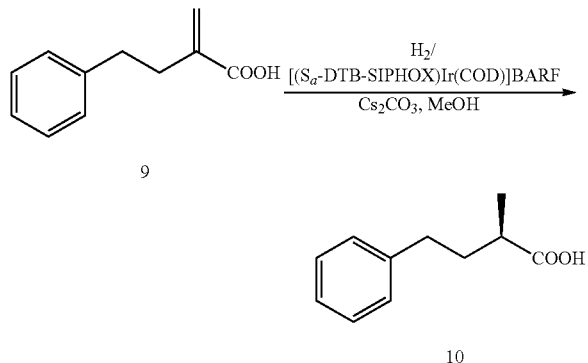

Embodiment 7: Asymmetric Catalytic Hydrogenation of 2-phenoxy acrylic acid

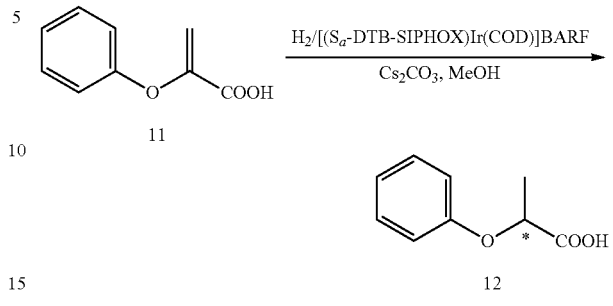

In the glove box, the catalyst [(S$_a$-DTB-SIPHOX)Ir(COD)]BARF 4 (2.4 mg, 0.00125 mmol), 2-phenylethyl acrylic acid 9 (88 mg, 0.5 mmol) and cesium carbonate (82 mg, 0.25 mmol) are weighted in the reaction inner tube with stirring bar, then the reaction inner tube is sealed for use. When the reaction inner tube is took out, anhydrous methanol (2 mL) is added with a syringe, then the inner tube is placed into the hydrogenation reactor, the mixture is stirred at room temperature under the hydrogen pressure of 0.6 Mpa to react for 24 h. Then the stirring is stopped, the hydrogen is released. After the system is condensed by evaporating off rotatably, the system is adjusted pH<3 with 3N hydrochloric acid water solution, extracted with diethyl ether (10 mL×3), and separated, the organic phase is collected, washed with saturated salt water, and dried with anhydrous sodium sulfate. The desiccant is removed by suction filtration, the solvent is evaporated off by rotating, then the object product 10 is obtained, and is a colorless oily liquid, through the $^1$H NMR analysis, the conversion rate is 100% and the yield is 94%. $[\alpha]_D^{20}$ −17.5 (c 0.9, CH$_2$Cl$_2$); $^1$H NMR (300 MHz, CDCl$_3$): δ 10.98 (br s, 1H, COOH), 7.24-7.09 (m, 5H, Ar—H), 2.60 (t, J=8.1 Hz, 2H, CH$_2$), 2.50-2.38 (m, 1H, CH), 2.04-1.91 (m, 1H, CH$_2$), 1.73-1.61 (m, 1H, CH$_2$), 1.16 (d, J=7.2 Hz, 3H, CH$_3$); after it is converted to phenyl amide, its ee value is 91% through the chiral SFC analysis.

Comparative Embodiment 1:

The chiral catalyst

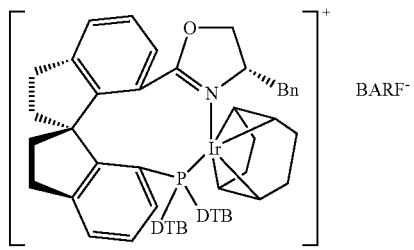

is used, the asymmetric catalytic hydrogenation of 2-phenylethyl acrylic acid 9 is carried out under the condition same to that of Embodiment 6, the result of the reaction is that: the conversion rate is 100%, the yield is 91% and the ee value of the product is 36%.

In the glove box, the catalyst [(S$_a$-DTB-SIPHOX)Ir(COD)]BARF 4 (4.8 mg, 0.0025 mmol), 2-phenoxy acrylic acid 11 (32 mg, 0.20 mmol) and cesium carbonate (41 mg, 0.125 mmol) are weighted in the reaction inner tube with stirring bar, then the reaction inner tube is sealed for use. When the reaction inner tube is took out, anhydrous methanol (2 mL) is added with a syringe, then the inner tube is placed into the hydrogenation reactor, the mixture is stirred at 30° C. under the hydrogen pressure of 0.6 Mpa to react for 24 h. Then the stirring is stopped, the hydrogen is released. After the system is condensed by evaporating off rotatably, it is transferred with 2N sodium hydroxide solution to a separatory funnel, and extracted with petroleum ether, and separated, the water phase is adjusted pH<3 with 3N hydrochloric acid water solution, extracted with diethyl ether (10 mL×3), and separated, the organic phase is collected, washed with saturated salt water, and dried with anhydrous sodium sulfate. The desiccant is removed by suction filtration, the solvent is evaporated off by rotating, then the object product is obtained, and is a white solid, through the $^1$H NMR analysis, the conversion rate is 100% and the yield is 90%. $^1$H NMR (400 MHz, CDCl$_3$): δ 7.70 (brs, 1H, COOH), 7.37-6.89 (m, 5H, Ar—H), 4.79 (sextet, J=6.8 Hz, 1H, CH), 1.67 (d, J=6.8 Hz, 3H, CH$_3$); after it is converted to phenyl amid; its ee value is 90% through the chiral SFC analysis.

We claim:

1. A spiro phosphine-oxazoline, having the following structure:

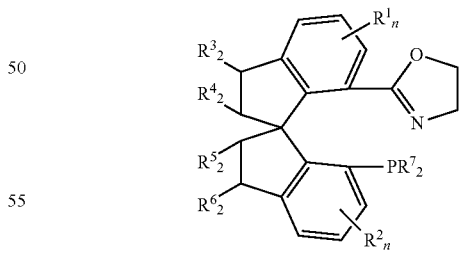

Wherein: n=0~3; $R^1$, $R^2$ are H, $C_1$~$C_8$ alkyl, halogenated alkyl, $C_1$~$C_8$ alkoxy, $C_2$~$C_8$ acyloxy, $C_1$~$C_8$ acyl, $C_2$~$C_8$ esteryl, ($C_1$~$C_8$ acyl) amino, di($C_1$~$C_8$ alkyl) amino, halogen, phenyl, $C_1$~$C_8$ alkyl-substituted phenyl, hydroxyl-substituted phenyl, $C_1$~$C_8$ alkoxy-substituted phenyl, $C_2$~$C_8$ acyloxy-substituted phenyl, halogenated phenyl, amino-substituted phenyl, ($C_1$~$C_8$ acyl) amino-substituted phenyl, di($C_1$~$C_8$ alkyl) amino-substituted phenyl, $C_1$~$C_8$ acyl-substituted phenyl, $C_2$~$C_8$ esteryl-substituted phenyl, naphthyl, furyl, thienyl, or combined alicyclic or aromatic ring when n≧2, respectively; $R^1$ and $R^2$ can be same or different;

$R^3$, $R^4$, $R^5$, $R^6$ are H, $C_1$~$C_8$ alkyl, halogenated alkyl, $C_1$~$C_8$ alkoxy, $C_2$~$C_8$ acyloxy, $C_1$~$C_8$ acyl, $C_2$~$C_8$ esteryl, ($C_1$~$C_8$ acyl) amino, di($C_1$~$C_8$ alkyl) amino, halogen, phenyl, $C_1$~$C_8$ alkyl-substituted phenyl, hydroxyl-substituted phenyl, $C_1$~$C_8$ alkoxy-substituted phenyl, $C_2$~$C_8$ acyloxy-substituted phenyl, halogenated phenyl, amino-substituted phenyl, ($C_1$~$C_8$ acyl) amino-substituted phenyl, di($C_1$~$C_8$ alkyl) amino-substituted phenyl, $C_1$~$C_8$ acyl-substituted phenyl, $C_2$~$C_8$ esteryl-substituted phenyl, naphthyl, furyl, thienyl, respectively or $R^3$~$R^4$, $R^5$~$R^6$ are combined alicyclic or aromatic ring; $R^3$, $R^4$, $R^5$, $R^6$ can be same or different;

$R^7$ is $C_1$~$C_8$ alkyl, phenyl, $C_1$~$C_8$ alkyl-substituted phenyl, hydroxyl-substituted phenyl, sulfo-substituted phenyl, $C_1$~$C_8$ alkoxy-substituted phenyl, $C_2$~$C_8$ acyloxy-substituted phenyl, halogenated phenyl, amino-substituted phenyl, ($C_1$~$C_8$ acyl) amino-substituted phenyl, di($C_1$~$C_8$ alkyl) amino-substituted phenyl, $C_1$~$C_8$ acyl-substituted phenyl, $C_2$~$C_8$ esteryl-substituted phenyl, naphthyl, furyl, thienyl.

2. The spiro phosphine-oxazoline according to claim 1, wherein:

The $C_1$~$C_8$ alkyl is methyl, ethyl, n-propyl, isopropyl, cyclopropyl, n-butyl, isobutyl, sec-butyl, tert-butyl, cyclobutyl, pentyl, isoamyl, neopentyl, sec-pentyl, tert pentyl, cyclopentyl,n-hexyl, isohexyl, neohexyl, sec-hexyl, tert-hexyl, cyclohexyl, n-heptyl, isoheptyl, neo-heptyl,sec-heptyl, tert-heptyl, cycloheptyl, n-octyl, isooctyl, neooctyl, sec-octyl, tert-octyl or cyclooctyl;

The $C_1$~$C_B$ alkoxy is methoxy, ethoxy, n-propoxy, isopropoxy, cyclopropoxy, n-butoxy, isobutoxy, sec-butoxy, tert-butoxy, cyclobutoxy, n-pentyloxy, isopentyloxy, neopentyloxy, sec-pentyloxy, tert-pentyloxy, cyclopentyloxy, n-hexyloxy, isohexyloxy, neohexyloxy, sec-hexyloxy, tert-hexyloxy, cyclohexyloxy, n-heptyloxy, isoheptyloxy, neoheptyloxy, sec-heptyloxy, tert-heptyloxy, cycloheptyloxy, n-octyloxy, iso-octyloxy, neooctyloxy, sec-octyloxy, tert-octyloxy, or cyclooctyloxy;

The $C_1$~$C_8$ acyl is formoxyl, acetyl, propionyl, n-butyryl, isobutyryl, n-valeryl, isovaleryl, sec-valeryl, neovaleryl, n-hexanoyl, isohexanoyl, neohexanoyl, sec-hexanoyl,n-heptanoyl, isoheptanoyl, neoheptanoyl, sec-heptanoyl, n-octanoyl, isooctanoyl, neooctanoyl, sec-octanoyl, 1-cyclopropyl formoxyl, 1-cyclobutyl formoxyl, 1-cyclopentyl formoxyl, 1-cyclohexyl formoxyl, 1-cycloheptyl formoxyl;

The $C_2$~$C_8$ acyloxy is acetoxyl, propionyloxy, n-butyryloxy, isobutyryloxy, n-valeryloxy, isovaleryloxy sec-valeryloxy, neovaleryloxy, n-hexanoyloxy, isohexanoyloxy, neohexanoyloxy, sec-hexanoyloxy, n-heptanoyloxy, isoheptanoyloxy, neoheptanoyloxy, sec-heptanoyloxy, n-octanoyloxy, isooctanoyloxy, neooctanoyloxy, sec-octanoyloxy, 1-cyclopropyl acetoxyl, 1-cyclobutyl acetoxyl, 1-cyclopentyl acetoxyl, 1-cyclohexyl acetoxyl, or 1-cycloheptyl acetoxyl;

The $C_2$~$C_8$ esteryl is methoxycarbonyl, ethoxycarbonyl, propoxycarbonyl, isopropoxycarbonyl, butoxycarbonyl, isobutoxycarbonyl, n-pentyloxycarbonyl, isopentyloxycarbonyl, neopentyloxycarbonyl, sec-pentyloxycarbonyl, tert-pentyloxycarbonyl, cyclopentyloxycarbonyl, n-hexyloxycarbonyl, isohexyloxycarbonyl, neohexyloxycarbonyl, sec-hexyloxycarbonyl, tert-hexyloxycarbonyl, cyclohexyloxycarbonyl, n-heptyloxycarbonyl, isoheptyloxycarbonyl, neoheptyloxycarbonyl, sec-heptyloxycarbonyl, tert-heptyloxycarbonyl, or cycloheptyloxycarbonyl;

The halogenated phenyl is a halogenated phenyl containing fluoride, chlorine, bromine or iodine.

3. The spiro phosphine-oxazoline according to claim 1, wherein it contains the raceme, dextroisomer and laevoisomer which have the same chemical structure formula but different three-dimensional structures and optical properties.

4. The spiro phosphine-oxazoline according to claim 1, wherein it is:

7-(4,5-dihydro-oxazole-2-base)-7'-di(3,5-di-tert-butylphenyl)phosphino-1,1'-Lo-dihydro-indene, 7-(4,5-dihydro-oxazole-2-base)-7'-diphenyl phosphino-1, 1'-Lo-dihydro-indene, 7-(4,5-dihydro-oxazole-2-base)-7'-di(4-methylpheny) phosphino-1,1'-Lo-dihydro-indene, 7-(4,5-dihydro-oxazole-2-base)-7'-di(4methoxyphenyl) phosphino-1,1'-Lo-dihydro-indene, 7-(4,5-dihydro-oxazole-2-base)-7'-di(3,5-dimethylphenyl) phosphino-1,1'-Lo-dihydro-indene, 7-(4,5-dihydro-oxazole-2-base)-7'-di(3,4,5-trimethyphenyl) phosphino-1,1'-Lo-dihydro-indene, 7-(4,5-dihydro-oxazole-2-base)-7'-di(3,5-dimethyl-4-methoxyphenyl) phosphino-1,1'-Lo-dihydro-indene, or 7-(4,5-dihydro-oxazole-2-base)-7'-di(3,5-di-tert-butyl-4-methoxyphenyl) phosphino-1,1'-Lo-dihydro-indene.

5. A preparation method of the spiro phosphine-oxazoline according to claim 1, comprising the following steps:

In one or several organic solvents of tetrahydrofuran, dioxane, tert-butyl methyl ether, ethylene glycol dimethyl ether, under the role of 1-hydroxy benzotriazole and N,N-dicyclohexyl carbimide, the substituted 7-diaryl phosphino-7'-carboxy-1,1'-Lo-dihydro-indene used as the starting raw material and amino ethanol are condensed, to obtain the corresponding amide alcohol compound;

Under the catalysis of N,N-dimethyl-4-aminopyridine, with triethylamine or diisopropyl ethyl amine as the acid binding agent, the amide alcohol compound obtained is reacted with methylsulfonyl chloride or p-toluene sulfonyl chloride, to obtain the novel spiro phosphine-oxazoline, and the solvent used is one or several of dichloromethane, chloroform or 1,2-dichloroethane, the specific reaction is:

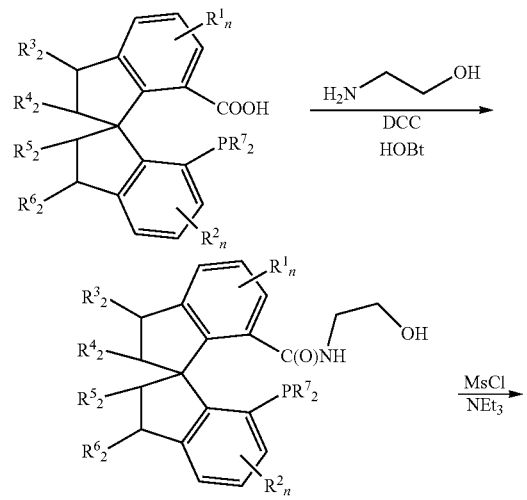

-continued

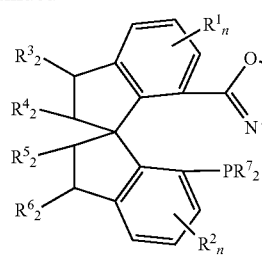

Wherein n=0~3; $R^1$, $R^2$, $R^3$, $R^4$, $R^5$, $R^6$, $R^7$ are defined as claim 1; DCC is N,N-dicyclohexyl carbimide; HOBt is 1-hydroxy benzotriazole; MsCl is methylsulfonyl chloride; $NEt_3$ is triethylamine.

6. An iridium complex of spiro phosphine-oxazoline prepared with the spiro phosphine-oxazoline according to claim 1, having the following structure:

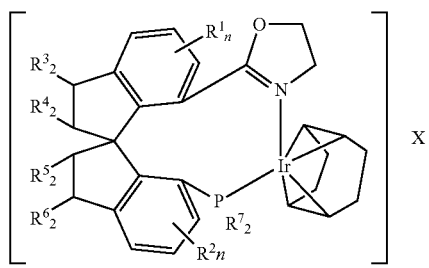

Wherein,

is cyclooctadiene; n=0~3; $R^1$, $R^2$, $R^3$, $R^4$, $R^5$, $R^6$, $R^7$ are defined as the compound (I); X is halogen, $C_1$~$C_8$ carboxylate radical, sulfate radical, tetra(3,5-bis trifluoromethylphenyl) borate radical, tetra(pentafluorophenyl) borate radical, tetra (perfluoro-tert-butoxy) aluminum ion, tetra(hexafluoroisopropoxy) aluminum ion, hexafluoro phosphate ion, hexafluoro antimonlate ion, tetrafluoro borate ion or trifluoro methanesulfonate ion; cyclooctadiene ligand can be substituted by ethylene or norbornadiene.

7. The iridium complex of spiro phosphine-oxazoline according to claim 6, wherein it is prepared through the following steps: the spiro phosphine-oxazoline, an iridium compound and sodium salt are reacted at 20~50° C. in one or several organic solvents of dichloromethane, chloroform or 1,2-dichloroethane), to obtain the product, and then through ion exchange, an iridium complex of spiro phosphine-oxazoline with different anions can be obtained:

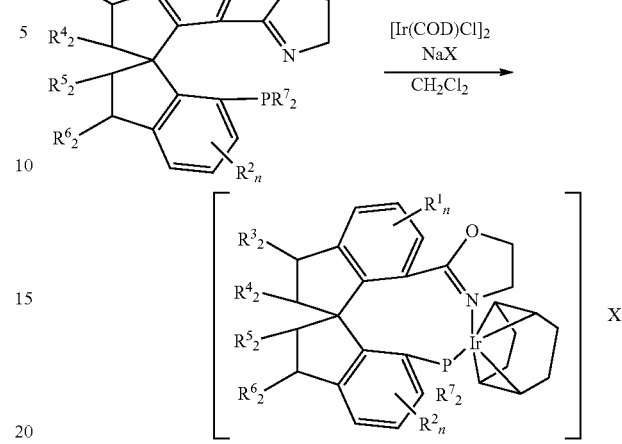

wherein n=0~3; $R^1$, $R^2$, $R^3$, $R^4$, $R^5$, $R^6$, $R^7$, X are defined as claim 6; COD is 1,5-cyclooctadiene; the cyclooctadiene ligand can be substituted by ethylene or norbornadiene, the sodium salt may be substituted by corresponding potassium salt, ammonium salt, silver salt or thallium salt.

8. A catalytic hydrogenation reaction process of α-substituted acrylic acid, comprising:
performing the reaction:

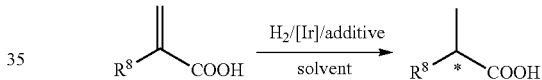

Wherein: [Ir] is the iridium complex of spiro phosphine-oxazoline according to claim 6 operates as a catalyst; $R^8$ is halogen, $C_1$~$C_8$ alkyl, halogenated alkyl, $C_1$~$C_8$ alkoxy, benzyloxy, phenoxy, $C_2$~$C_8$ acyloxy, $C_1$~$C_8$ acyl, $C_2$~$C_8$ esteryl, ($C_1$~$C_8$ acyl) amino, di($C_1$~$C_8$ alkyl) amino, benzyl, phenemyl, phenyl, $C_1$~$C_8$ alkyl-substituted phenyl, hydroxyl-substituted phenyl, $C_1$~$C_8$ alkoxy-substituted phenyl, $C_2$~$C_8$ acyloxy-substituted phenyl, halogenated phenyl, amino-substituted phenyl, ($C_1$~$C_8$ acyl) amino-substituted phenyl, di($C_1$~$C_8$ alkyl) amino-substituted phenyl, $C_1$~$C_8$ acyl-substituted phenyl, $C_2$~$C_8$ esteryl-substituted phenyl, naphthyl, furyl, thienyl; the position marked by the asterisk is the chiral center;

Wherein under the protection of argon or nitrogen, the catalyst and the substrate are added into the inner tube of the reactor, then the additive and the solvent are added, the reactor is sealed and the air in the reactor is replaced with hydrogen for 3 to 5 times, then the reactor is filled with hydrogen, and the mixture is stirred to the end;

The catalytic hydrogenation reaction process has a reaction condition that is: the solvent used is $C_1$~$C_6$ alcohol; the amount of the catalyst is 0.001 ~1 mol %; the concentration of the substrate is 0.001 ~10.0 M; the additive is one or several of isopropylamine, tert-butylamine, dimethylamine, diethyl amine, diisopropylamine, diisopropyl ethylamine, trimethylamine, triethylamine, 1,8-diazabicyclo[5,4,0]undec-7-ene, 1,4-diazabicyclo[2,2,2]octane, sodium hydride, sodium hydroxide, sodium carbonate, sodium bicarbonate, sodium tert-butyl alcohol, potassium hydroxide, potassium carbonate, potassium bicarbonate, potassium tert-butyl alcohol, cesium hydroxide, cesium carbonate; the reaction temperature is 0 ~100 Mpa; the hydrogen pressure is 0.1 ~10 Mpa; the reaction time is 0.5 ~48 h.

9. The process according to claim 8, wherein the solvent is methanol; the additive is triethylamine or cesium carbonate; the α,β-unsaturated carboxylic acid is: 2-(4-isobutyl-phenyl) acrylic acid, 2-benzyl acrylic acid, 2-phenylethyl acrylic acid or 2-phenoxy acrylic acid.

* * * * *